(12) United States Patent
Mueller-Hartmann

(10) Patent No.: US 7,732,175 B2
(45) Date of Patent: Jun. 8, 2010

(54) METHOD AND CIRCUIT ARRANGEMENT FOR TREATING BIOMATERIAL

(75) Inventor: Herbert Mueller-Hartmann, Köeln (DE)

(73) Assignee: Lonza Cologne AG (DE)

(*) Notice: Subject to any disclaimer, the term of this patent is extended or adjusted under 35 U.S.C. 154(b) by 1254 days.

(21) Appl. No.: 11/151,643

(22) Filed: Jun. 14, 2005

(65) Prior Publication Data
US 2006/0094095 A1 May 4, 2006

(30) Foreign Application Priority Data
Jun. 14, 2004 (EP) .................... 04013843

(51) Int. Cl.
C12N 13/00 (2006.01)
(52) U.S. Cl. ............... 435/173.6; 435/173.8; 435/461; 800/292
(58) Field of Classification Search ............ 435/173.6, 435/173.8, 461, 173.4, 173.5, 285.2, 285.3, 435/286.1; 800/292
See application file for complete search history.

(56) References Cited

U.S. PATENT DOCUMENTS

| | | |
|---|---|---|
| 3,707,974 A | 1/1973 | Raddi |
| 4,750,100 A | 6/1988 | Ragsdale |
| 4,849,355 A | 7/1989 | Wong |
| 4,906,576 A | 3/1990 | Marshall |
| 4,923,814 A | 5/1990 | Marshall |
| 4,946,793 A | 8/1990 | Marshall |
| 4,959,321 A | 9/1990 | Preece et al. |
| 5,098,843 A | 3/1992 | Calvin |
| 5,128,257 A | 7/1992 | Baer |
| 5,232,856 A | 8/1993 | Firth |
| 5,254,081 A | 10/1993 | Maurer et al. |
| 5,273,525 A | 12/1993 | Hoffmann |

(Continued)

FOREIGN PATENT DOCUMENTS

DE  3718941 A1  2/1988

(Continued)

OTHER PUBLICATIONS

Sukharev S.I. et al., Electroporation and electrophoretic DNA transfer into cells. The effect of DNA interaction with electropores. Biophysical Journal, vol. 63, 1320-1327 (1992).

(Continued)

*Primary Examiner*—William H Beisner
*Assistant Examiner*—Michael Hobbs
(74) *Attorney, Agent, or Firm*—Joyce v. Natzmer; Pequignot + Myers

(57) ABSTRACT

The invention relates to a method for treating biomaterial using at least one electrical field generated by a first voltage pulse which is terminated once the value for an electrical parameter has exceeded or dropped below a preset limit. After the first voltage pulse has been terminated, it is continued by an additional voltage pulse. The invention also relates to a circuit arrangement comprising at least one storage device for electrical charges to generate at least one voltage pulse by selectively discharging the storage device, and at least one control unit for controlling the discharge. The present invention provides a controller for monitoring the chronological progression of the voltage pulse. This controller controls at least one continuation of discharge after termination.

10 Claims, 5 Drawing Sheets

U.S. PATENT DOCUMENTS

| | | | |
|---|---|---|---|
| 5,422,272 | A | 6/1995 | Papp et al. |
| 5,627,023 | A | 5/1997 | Bolognesi |
| 5,642,035 | A | 6/1997 | Ragsdale |
| 5,869,326 | A | 2/1999 | Hoffmann |
| 5,905,371 | A | 5/1999 | Limpaecher |
| 6,008,038 | A | 12/1999 | Kroeger et al. |
| 6,040,184 | A | 3/2000 | Greener et al. |
| 6,103,084 | A | 8/2000 | Uhen |
| 6,150,148 | A | 11/2000 | Nanda et al. |
| 6,258,592 | B1 | 7/2001 | Ragsdale et al. |
| 6,521,430 | B1 | 2/2003 | Orwar |
| 6,632,672 | B2 | 10/2003 | Calos |
| 2003/0139889 | A1 | 7/2003 | Ragsdale et al. |
| 2004/0137603 | A1 | 7/2004 | Mueller-Hartmann et al. |

FOREIGN PATENT DOCUMENTS

| | | |
|---|---|---|
| DE | 3724291 A1 | 2/1989 |
| EP | 0113549 A1 | 7/1984 |
| EP | 0283700 A2 | 9/1988 |
| EP | 0362758 A2 | 4/1990 |
| EP | 0689289 A2 | 12/1995 |
| EP | 0866123 B1 | 9/1998 |
| EP | 1190075 B1 | 3/2002 |
| EP | 1383901 B | 1/2004 |
| JP | 2035071 | 2/1990 |
| JP | 2303478 | 12/1990 |
| JP | 3195485 | 8/1991 |
| WO | 8802777 A1 | 4/1988 |
| WO | 9118103 A1 | 11/1991 |
| WO | 92/06185 A1 | 4/1992 |
| WO | 95/35389 A1 | 12/1995 |
| WO | 98/10515 A1 | 3/1998 |
| WO | 99/36563 A1 | 7/1999 |
| WO | WO 02/086129 A1 | 10/2002 |
| WO | WO 03/050546 A | 6/2003 |
| WO | WO 03/076006 A2 | 9/2003 |

OTHER PUBLICATIONS

Leopold R.A. et al., Using electroporation and a slot cuvette to deliver plasmid DNA to insect embryos. Genet Anal. Mar;12(5-6):197-200 (1996).

Brown L.E. et al., Introduction of exogenous DNA into Chlamydomonas reinhardtii by electroporation. Mol Cell Biol. Apr;11(4):2328-32 (1991).

Auer et al, "Dielectric breakdown of the red blood cell membrane and uptake of SV40 DNA and mammallan RNA," in Naturwissenschaften, vol. 63, pp. 391, 1976.

Bamberger et al: "Dissoclative Glucocorticotd Activity of Medroxyprogesterone Acetate in Normal Human Lymphocytes," in Journal of Clinical Endocrinology & Metabollsm, vol. 84, pp. 4055-4061, 1999.

Baubonis et al, "Genomic targetlng wilh purified Cre recombinase," in Nuclelo Acids Research, vol. 21, No. 9, pp. 2025-2029, May 1993.

Bertling et al: "Intranuclear uptake and persistance of biologlcally actlve DNA after electroporation of mammalian cells," in J. Biochern. Biophys, Methods, vol. 14(4), pp. 223-232, 1987.

Bertling: "Transfection of a DNA/protein complex into nuclei of mammallan cells using polyoma capslds and electroporation," in Biosci. Rep., vol. 7, No. 2, pp. 107-112, Feb. 1987.

De Chasseval et al: "High level translent gene expression in human lymphoid cells by SV 40 large T antigen boost," in Nucleic Acids Res,, vol. 20 (2), pp. 245-250, 1992.

Edelstein et al: "Gene therapy clinical trials worldwide 1989-2004- an overview," in J. Gene Med., vol. 6, No. 6, pp. 597-602, Jun. 2004.

Eurogentec: "Easyjet Plus User's Manual," in Eurogantec, Liege, pp. 1-27 and 30-39, Jul. 10, 1992.

Kim et al: "Electroporation of extraneous proteins into CHO cells: increased efficacy by utilizing centrifugal force and microsecond electrical pulsea," in Exp, Cell Res., vol. 197(2). pp. 207-212, 1991.

Klenchin et al, "Electrically Induced DNA uptake by cells is a fast process Involving DNA electrophoresis," in Biophys. J., vol. 60, No. 4, pp. 804-811, Oct. 1991.

Krueger et al: "Transient Transfection of Oligodendrocyte Progenitors by Electroporatlon", in Neurochemical Research, vol. 23, pp. 421-426, 1998.

Lurquin: "Gene transfer by electroporation" in Mol. Biotechnol., vol. 7(1), pp. 5-35, Feb. 1997.

Luo et al:"Synthetic DNA delivery systems" in Nature Biotechnology, vol. 18, No. 1, pp. 33-37, Jan. 2000.

Marechal et al.: "Mapplng EBNA-1 domains Involved in binding to metaphase chromosomes" in J. Virol., vol. 73, pp. 4385-4392, 1999.

Neumann et al: "Permeabillty changes induced by electric Impulses in vesicular membranes" in J. Membrane Biol., vol. 10, pp. 279-290, 1972.

Neumann et al.: "Gene transfer Into mouse lyoms cells by electroporation in high electric fields" in The EMBO Journal, vol. 1(7), pp. 841-845, 1982.

Palu et al.: "In pursuit of new developments for gene therapy of human diseases" in J. Biotechnol., vol. 68, No. 1, pp. 1-13, Feb. 1999.

Pliquett et al.: "Determination of the electric field and anomalous heating caused by exponential pulses with aluminum elctrodes in electroporatlon experiments" in Bioelectrochemistry and Bioenergetics, vol. 39(1), pp. 39-53, 1996.

Potter et al.: "Enhancer-dependent expression of human kappa Immunoglobulin genes Introduced into mouse pre-B lymphocytes by electroporation" in Proc. Natl Acad. Sci. USA. vol. 81(22), pp. 7161-7165, 1984.

Rols et al.: "Ionlo-strength modulatlon of eletrically Induced permeabilization and associated fuslon of mammallan cells" in Eur. J. Biochem. vol. 178, pp. 109-115, 1989.

Satoh et al.: "Successful transfer of ADA gene in vitro Into human peripheral blood CD34+ cells by transfooting EBV-based episomal vectors" in FEBS Lett., vol. 441, No. 1, pp. 39-42, Dec. 1998.

Schwachtgen et al.: "Optimization of the transfection of hurnan endothelial cells by electroporatlon" in Biotechniques. vol. 17(5), pp. 880-887, 1994.

Verma et al.: "Gene therapy—promises, problems and prospects" in Nature, vol. 389. No. 6648, pp. 239-242, Sep. 1997.

Watanabe et al.: "Calcium phosphato-modlated transfection of primary cultured brain neurons using GFP expression as a marker. application for single neuron electrophysiology," in Neuroscience Rasearch, vol. 33, pp. 71-78, 1999.

Zimmermann et al.: "Cells with manipulated functlons: new perspectives for cell biology, medicine and technology," in Angew. Chem. Int. Ed. Engl., vol. 20, pp. 325-344, 1981.

Ratajczak et al.: "Heterogeneous Populations of Bone Marrow Stem Cells—Are We Spotting on the Same Cells from the Different Angles?" in Folia Histochemica Et Cytobiologica, vol. 42, No. 3, pp. 139-146, 2004.

METHOD AND CIRCUIT ARRANGEMENT FOR TREATING BIOMATERIAL

This application claims priority to European Patent Application No. 04013843.0, filed Jun. 14, 2004, which is incorporated herein by reference in its entirety.

BACKGROUND OF THE INVENTION

The invention relates to a method for treating biomaterial using at least one electrical field generated by a first voltage pulse which is terminated once the value for an electrical parameter has exceeded or dropped below a preset limit, as well as to a circuit arrangement, in particular for carrying out said method, comprising at least one storage device for electrical charges to generate at least one voltage pulse by selectively discharging the storage device, and at least one control unit for controlling the discharge. The present invention relates in particular to the field of electroporation, electrofusion and electrostimulation of living cells, as well as to all applications in which biomaterial must be exposed to an electrical field.

The introduction of bioactive molecules, e.g., DNA, RNA or proteins, into living cells is an important tool in studying the biological functions of these molecules. One preferred method for introducing foreign molecules into cells here is electroporation, which does, as opposed to chemical methods, not rely on the simultaneous transport of other bioactive molecules. In electroporation, the foreign molecules are taken from a buffer solution adapted to the cells or a cell culture medium and introduced into the cells in a brief flow of current, wherein exposure to the short electrical voltage pulses or resultant electrical field makes the cell membrane permeable to the foreign molecules. The cell suspension is here often in a so-called cuvette, i.e., a narrow flask open at the top, which has two opposing, parallel electrodes in the lateral walls in proximity to its floor, which are used to apply an electrical voltage. Through the briefly arising "pores" in the cell membrane the bioactive molecules initially enter the cytoplasm, where they can already perform the function to be studied, and then, under certain conditions, also the cell nucleus.

Briefly applying a strong electrical field, i.e., a short voltage pulse with a high current density, also makes it possible to fuse cells, cell derivates, sub-cellular particles and/or vesicles. During this so-called electrofusion, the cells are, for example, initially brought into close membrane contact by an inhomogeneous electrical alternating field. The subsequent application of an electrical field pulse then causes the membrane sections to interact, finally resulting in fusion. Industrial equipment comparable to that used for electroporation can here be used for electrofusion. Further, living cells can also be stimulated by electrical fields in such a way as to change their properties.

If, in the process of establishing an electrical field with a field strength of several hundred volts per centimeter in an aqueous solution, the electrical resistance collapses in a very short time, e.g., under 1 µs, thereby causing the current to rise very rapidly and sharply, a so-called lightning discharge can occur. During a lightning discharge, the brief rise in power or heat leads to concomitant physical phenomena, such as lightning, cracking and spraying of the solution on the one hand, and irreversible damaging or killing of the cells on the other hand. Therefore, a lightning discharge generally endangers not only the safety of people and equipment in the vicinity, but also results in a loss of the used biomaterial.

WO 02/086129 A1 discloses a circuit arrangement for introducing bioactive molecules into the cell nucleus of eukaryotic cells by means of an electrical current, or for treating cells, cell derivates, sub-cellular particles and/or vesicles with electrical current, as well as a corresponding method. The circuit arrangement consists of two storage devices for electrical charges, which are each supplied by a high voltage power supply. The storage devices are each connected to a power semiconductor for transmitting the charges present in the storage devices to a cell suspension. The power semiconductors are actuated and switched via a control device. This circuit arrangement further provides for that at least a first voltage pulse can be transmitted to the cell suspension with the capacitor voltage of the storage device by actuating a power semiconductor for a preset time ($T_1$). To further enhance the safety of the user and used samples, it is provided that an overcurrent switching module enables overvoltage deactivation at least for the first voltage pulse, terminating the respective pulse. Therefore, overcurrent deactivation makes it possible to terminate the voltage pulse in a case where preset limits have been exceeded. For example, if the current rises too precipitously while establishing an electrical field, a lightning discharge, and hence cell damage, can be prevented by terminating the voltage pulse. However, depending on the point of termination, the disadvantage of this is that successful treatment is not achieved, e.g., the transfection efficiency is too low. If the voltage pulse is terminated too early, the corresponding reaction batch must be discarded or can only be used to a very limited extent, even though cell viability has been obtained.

There is therefore a need for a method and a circuit arrangement of the kind mentioned at the outset that enable the successful treatment of biomaterial even if the first voltage pulse has been terminated.

SUMMARY OF THE INVENTION

In view of the above, the method of the invention continues the first voltage pulse after termination by at least one additional voltage pulse. It has surprisingly been shown that successful cell treatment can indeed be ensured by continuing the terminated voltage pulse. The additional voltage pulse again exposes the cells to an electrical field, which preferably corresponds to the one generated by the first voltage pulse, so that the suspended cell treatment can be continued, and the desired success can still be achieved. The method according to the invention makes it possible to significantly increase, e.g., in an electroporation, transfection efficiency during the transfection of eukaryotic cells with nucleic acids by continuing or repeating the voltage pulse after a lightning discharge. Thus and advantageously, the method according to the invention can avoid or offset that unpredictable and irreproducible results caused by the randomly arising termination of a voltage pulse. Possible electrical parameters that might trigger a voltage pulse termination are the slope of a voltage drop (flank), a collapsed resistance, current density or the slope of a current rise (flank).

In one particularly advantageous embodiment of the invention, a specific duration T1 is preset for the first voltage pulse, and the duration T2 of the additional voltage pulse is at least equal to the duration T1 minus the time Tx lying between the beginning of the first voltage pulse and the termination thereof. This ensures that the cells are exposed to the electrical field for the same total time as provided for the first voltage pulse. For example, if a duration T1=500 µs is preset for the first voltage pulse, but terminated for threat of a lightning discharge after a time of Tx=100 µs, the duration T2 of the additional voltage pulse is advantageously calculated from T2=T1−Tx, i.e., resulting in 400 μs as the duration for T2. Hence, the additional voltage pulse continues the first voltage pulse in such a way that the cells are exposed to the electrical field for the originally set or prescribed total duration of 500 μs. This prevents the cells from becoming damaged by treating them too long on the one hand, while ensuring that the results are reproducible on the other. As an alternative, the duration T2 can also be longer than duration T1 minus the time Tx lying between the beginning of the first voltage pulse and the termination thereof, i.e., T2>T1−Tx. At a duration of T1=500 μs and a time to termination of Tx=100 μs, a duration of, for example, T2=600 μs can also be selected for the additional voltage pulse. As a result, potential losses or disadvantages owing to the pause between the termination of the first voltage pulse and the initiation of the additional voltage pulse can be offset, which also has a positive impact on the achieved results.

A duration ranging from 10 μs to 1 ms can be selected as T1, for example.

In another advantageous embodiment of the invention, the same field strength as for the first voltage pulse is preset as the field strength of the additional voltage pulse. This ensures that the cells are treated under constant conditions, and that the additional voltage pulse(s) represent(s) a continuation of the first voltage pulse. This also has a positive impact on the reproducibility of the results.

Preferably and depending on the application, a field strength of 2 to 10 KV/cm is preferably preset. However, lower or higher field strengths can also be set for special applications or cell types.

In a special embodiment of the invention, a specific pause time is preset between the termination of the first voltage pulse and the generation of the additional voltage pulse, preferably a time of at least 40 μs, more preferably 50 to 600 μs, in particular 100 μs. Specifically setting the pause time makes it possible to adjust the method according to the invention to the type of application, the desired goal and/or the cell type, thereby allowing for an optimization of results. It is generally particularly advantageous here for the pause time to measure at least 40 μs, so that conditions inside the reaction batch can, on the one hand, normalize after the brief current rise and termination event, and, on the other hand, the cells have a short "recovery phase."

In one advantageous embodiment of the invention, it is further provided that a total of at least two additional voltage pulses are generated if the preceding additional voltage pulses have been terminated. This embodiment also focuses on the possibility that the additional voltage pulse or several of the additional voltage pulses can be terminated as a result of an electrical parameter exceeding or dropping below a limit. Enabling several repeat attempts further improves the method according to the invention, since the probability of an ultimately flawed test or incomplete treatment can be tangibly reduced. Preferably, the capability to generate 2 or 3 additional voltage pulses is hereby prescribed or set. After termination of the additional voltage pulse, another additional voltage pulse can hence be initiated (2 additional voltage pulses, n=2). If even the latter one is terminated, a third additional voltage pulse is generated (3 additional voltage pulses, n=3). However, this case involves the preset capability of further additional voltage pulses. By contrast, once the preset duration T1 has been reached as a whole, no additional voltage pulses can be initiated.

In cases where several additional voltage pulses are possible, and a specific duration T1 is preset for the first voltage pulse, it is advantageous if the overall duration Ts of the additional voltage pulses is at least equal to the duration T1 minus the time Tx lying between the beginning of the first voltage pulse and the termination thereof. This ensures, also in this embodiment, that the cells are exposed to the electrical field for the same total time as provided for the first voltage pulse. For example, if a duration T1=800 μs is preset for the first voltage pulse, but terminated for threat of a lightning discharge after a time of Tx=250 μs, the duration T2 of the additional voltage pulse is calculated from T2=T1−Tx, i.e., resulting in 550 μs as the duration of T2. However, if the additional voltage pulse is also terminated after a period Ty=350 μs, a duration of T3=T1−(Tx+Ty) or T3=T2−Ty is obtained for the other additional voltage pulse as duration T3, i.e., T3=200 μs. The sum Ts=Ty+T3 (=T1−Tx) hence yields 550 μs, so that the cells are exposed to an electrical field for a total of 800 μs (=T1). Therefore, the additional voltage pulses continue the first voltage pulse in such a way that the cells are exposed to the electrical field for the originally set or preset total duration (T1=Tx+Ty+ . . . +Tn). In this embodiment as well, the above prevents the cells from becoming damaged by excessively long treatment on the one hand, and ensures that the results are reproducible on the other. As an alternative, the duration Ts can also be longer than the duration T1 minus the time Tx lying between the beginning of the first voltage pulse and the termination thereof, i.e., Ts>T1−Tx. At a duration T1=800 μs and a time to termination of the first voltage pulse of Tx=250 μs and a time to termination of the additional voltage pulse Ty=350 μs, a duration of, for example, T3=300 μs can also be selected as the duration for the other additional voltage pulse. As a result, potential losses or disadvantages owing to the pauses between the terminations of the voltage pulses and the initiation of the additional voltage pulses can be offset, which also has a positive impact on the achieved results.

In view of the above, the circuit arrangement of the present invention preferably provides at least one controller to monitor the chronological progression of the voltage pulse, said controller controlling at least one continuation of discharge after termination. Introducing an additional controller into the circuit arrangement to monitor the chronological progression of the first (and any additional) voltage pulse(s) makes it possible to calculate the remaining duration of the additional voltage pulse or additional voltage pulses (T2=T1−Tx or T3=T1−(Tx+Ty), etc.) during which, following the termination, a voltage was no longer applied. After a preset or programmable pause, the controller can control the storage device discharge in such a way as to continue it, and thereby complete the discharge time. Hence, the control unit is designed in such a way that it monitors the time elapsed from the beginning of the first voltage pulse and any additional voltage pulses until the termination of the latter, along with the still remaining duration of the additional voltage pulse (T2=T1−Tx or T3=T1−(Tx+Ty), etc.). In this way, the process of discharging the storage device can be controlled by the controller in such a way that the first voltage pulse can be continued or completed, so that the biomaterial can be treated successfully and reproducibly even though one or several voltage pulses have been terminated.

In a special embodiment of the invention it is provided that the controller is an analog signal-processing module, preferably a capacitor. Here, for example, a capacitor performs the task to integrate the duration of voltage applied. The capacitor is charged only while voltage is applied. A hardware-controlled interval timer then allows to close the circuit again as long as the capacitor is not yet completely charged or has not reached a threshold value.

A preferred embodiment of the invention provides that the controller is a digital signal-processing module, e.g., a DSP. A DSP (digital signal processing) module, e.g., which controls a switching device, makes it possible to monitor the chronological progression of the first voltage pulse or the additional voltage pulses. The DSP module detects the termination of the voltage pulse which is terminated by a control unit. The DSP module calculates the remaining time for which no more voltage was applied. After a programmable pause, the DSP can then control the switching device in such a way as to continue the storage device discharge, e.g., via a control action from the control unit.

In a preferred embodiment of the circuit arrangement according to the invention, the controller and/or the control unit can be connected with a switching device. This switching device is connected with a voltage switch, preferably by means of a potential divider stage. The storage device is connected with a power semiconductor, via which the storage device is discharged. If the voltage switch is also connected with the power semiconductor, the process of discharging the storage device can hence be controlled via the controller and/or control unit. Because the controller is connected with the switching device, the controller can monitor the chronological progression of the discharge process by checking and determining the switching status of the switching device, and therefore determine the duration of the respective voltage pulse.

In an advantageous embodiment of the invention, the switching device can be switched via the control unit, i.e., the control unit can open and close the switching device, so that the power semiconductor connected with the storage device is ultimately opened or closed, thereby controlling the storage device discharge process. The control unit may have a disconnecting device that terminates the discharge process once a value for an electrical parameter has exceeded or dropped below a preset limit. Electrical parameters can here include the slope of a voltage drop (flank), a collapsed resistance, current density or the slope of a current rise (flank). Therefore, if a value exceeds or drops below a preset limit for one of these parameters, the disconnecting device switches the switching device in such a way as to terminate the storage device discharge process. For example, given the danger of lightning discharge, the slope of the current strength rise can be measured in a very short time interval, and the voltage pulse can be terminated by the control unit or disconnecting device (flank deactivation) if a preset limit has been exceeded.

The switching device can also be directly switched by the controller, so that the latter can control the storage device discharge process by switching the switching device. Hence, via the switching device, the controller cannot just monitor the chronological progression of the respective voltage pulse, but also initiate the additional voltage pulses. The discharge is preferably controlled via the controller, but also via the control unit.

The invention further comprises a program element that can be read and executed via an electronic data processor and, when executed, is able to perform the method according to the invention, along with a program element that can be read and executed via an electronic data processor, and when executed, is able to control the circuit arrangement according to the invention. Hence, the overall invention also comprises computer programs that control the method according to the invention and/or the circuit arrangement according to the invention. The program elements are hereby preferably stored in a storage unit of an apparatus (electroporator), which also incorporates the circuit arrangement according to the invention. A suitable processor can hereby access the program elements, and either process or execute the latter.

The invention also comprises any storage medium that can be read via an electronic data processor, and in which one or both of the specified program elements is/are stored.

The method according to the invention and the circuit arrangement according to the invention can be used or are suitable in an advantageous manner for the transfection of resting or actively dividing eukaryotic cells. In like manner, they are suitable for the transfection of primary cells, such as cells in human blood, pluripotent precursor cells in human blood, primary human fibroblasts, endothelial cells, muscle cells or melanocytes, and can be employed for analytical or diagnostic purposes, or for manufacturing a pharmaceutical for ex-vivo gene therapy.

The method according to the invention and circuit arrangement according to the invention are additionally suited for, for example, electrofusion, i.e., processes for fusing cells, cell derivates, sub-cellular particles and/or vesicles by means of an electrical current, in which the cells, cell derivates, sub-cellular particles and/or vesicles are first suspended in an aqueous solution in an expedient density, after which the suspension is transferred to a cuvette, and an electrical voltage is finally applied to the electrodes of the cuvette, and a flow of current is generated through the suspension. As an alternative, for example, it is possible to fuse adherent cells, cell derivates, sub-cellular particles and/or vesicles, or adherent cells with suspended cells, cell derivates, sub-cellular particles or vesicles.

The term "biomaterial" comprises cells, cell derivates, sub-cellular particles and vesicles, as well as nucleic acids, peptides, proteins, polysaccharides, lipids or combinations or derivatives of these molecules.

The term "bioactive molecules" comprises nucleic acids, peptides, proteins, polysaccharides, lipids or combinations or derivatives of these molecules, as long as they exhibit bioactivity in cells, cell derivates, sub-cellular particles or vesicles.

Suitable containers for holding the biomaterial or reaction batches include cuvettes with an electrode spacing of 2 mm or 1 mm, e.g., commercially available cuvettes for electroporation.

BRIEF DESCRIPTION OF THE DRAWINGS

The invention is described by example below in detail with reference to the drawings.

In the figures

DESCRIPTION OF VARIOUS AND PREFERRED EMBODIMENTS OF THE INVENTION

Figure 1:
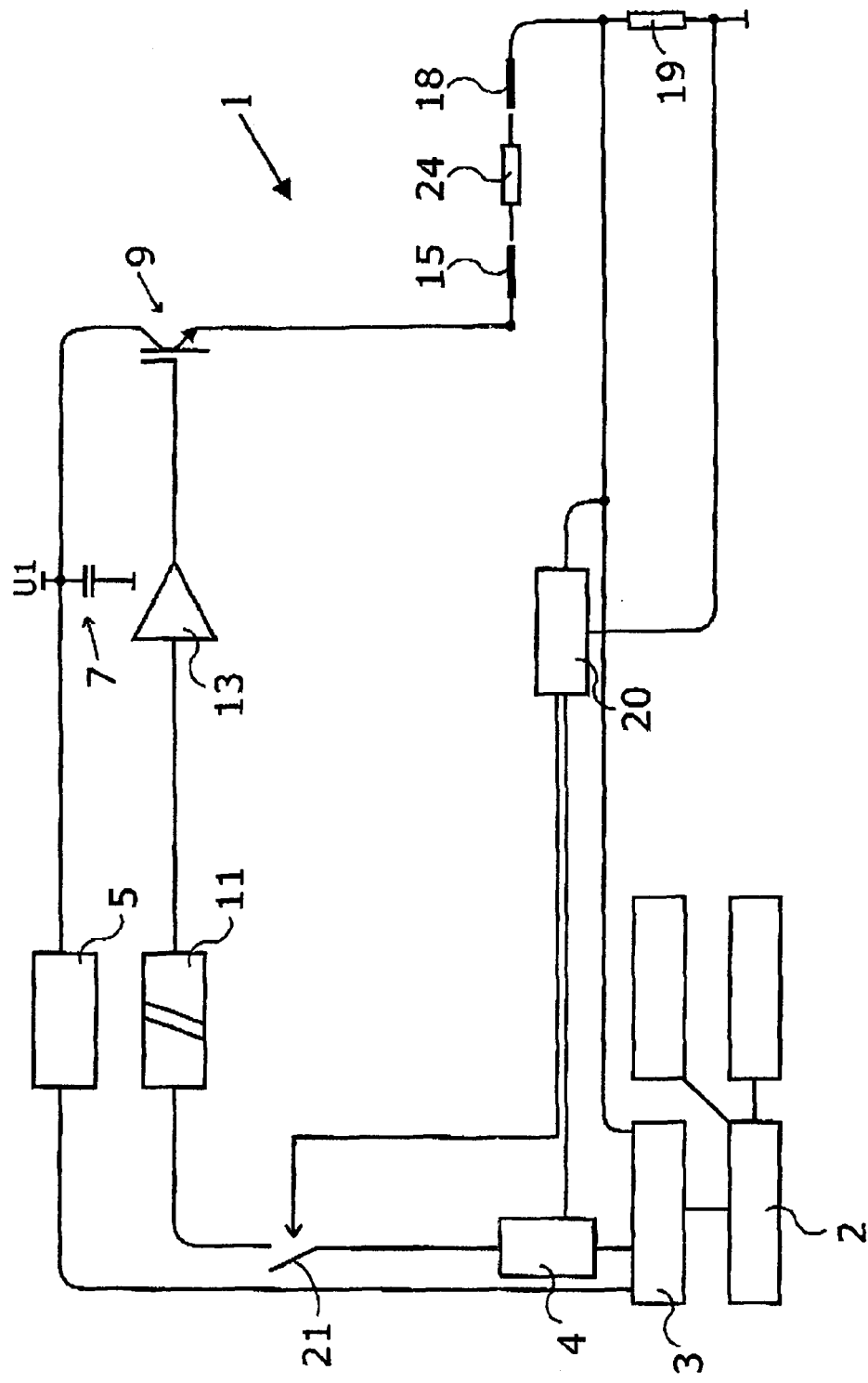
FIG. 1 is a block diagram of a circuit arrangement according to the invention.

FIG. 1 shows a block diagram of a circuit arrangement 1 according to the invention with an adjustment unit 2 for inputting parameters to be preset, a central controlling device 3 for controlling the circuit arrangement 1, and a high-voltage power supply 5. The high-voltage power supply 5 feeds a downstream storage device 7, which can be a capacitor or group of capacitors, for example, which can be charged with a voltage U1. The storage device 7 is connected with a power semiconductor 9 to emit a voltage pulse (U1) or discharge the storage device 7. The power semiconductor 9 can be actuated, here via a potential divider stage 11, by way of a voltage switch 13 via the controlling device 3, a control unit 20 and a controller 4. The storage device 7 is directly connected with the input of the power semiconductor 9, wherein the power semiconductor 9 can, for example, consist of an IGBT. However, the term "power semiconductor" is also meant to encompass all other electronic components or component arrangements that can be used to switch voltages and currents that are to be switched with the necessary switching times. The output of the power semiconductor 9 is directly connected with a cuvette terminal 15. The cuvette 24 is a reaction vessel used to hold an aqueous solution and the biomaterial to be treated and in which the electrical field is generated. A second cuvette terminal 18 is connected to ground via a resistor 19. The resistor 19 is a measuring shunt, e.g., for use in measuring the voltage drop and routing it to the control unit 20. The control unit 20 can terminate the voltage pulse via an switching device 21 by way of the potential divider stage 11 and voltage switch 13. For example, if an electrical parameter exceeds or drops below a preset limit, a disconnecting device (not shown here) arranged in the control unit 20 switches the switching device 21 in such a way as to terminate the discharge of the storage device 7. For example, given the danger of lightning discharge, the slope of the current strength rise can be measured in a very short time interval, and the voltage pulse can be terminated by the control unit 20 or by the disconnecting device if a preset limit has been exceeded (flank deactivation). According to the invention, the switching device 21 can be switched via the controller 4, so that the latter can control the process of discharging the storage device 7 by switching the switching device 21. Hence, the controller 4 can monitor the chronological progression of the respective voltage pulse, i.e., the time at which a pulse was terminated, and calculate the duration of the additional voltage pulse on the one hand, and trigger the additional voltage pulses by triggering the switching device 21 on the other. The discharge process is hereby controlled via the controller 4, preferably indirectly via the control unit 20. As an alternative, however, the controller 4 can directly control the switching device 21. In the case of the control unit 20, the low-ohm measuring resistor 19 lies behind the cuvette terminals 15, 18, and is wired to ground, making it possible to preclude the transmission of high-voltage pluses. The storage device 7 can encompass several capacitors with the required capacity and breakdown voltage, so that a correspondingly high charge can be stored and transmitted to the cuvette terminal 15.

Figure 2:
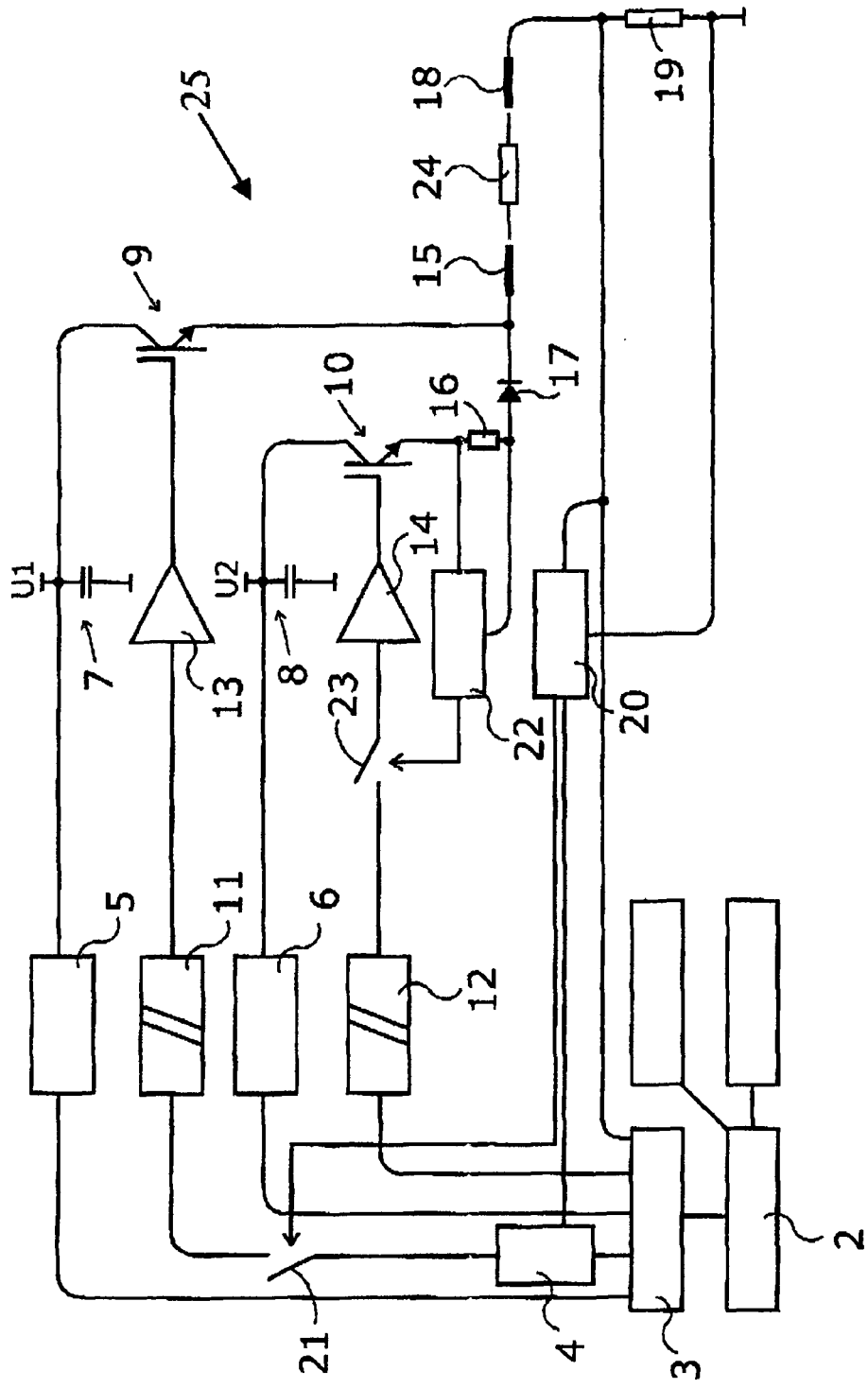
FIG. 2 is a block diagram of a special embodiment of a circuit arrangement according to the invention.

FIG. 2 shows a block diagram of a special embodiment of a circuit arrangement 25 according to the invention, which essentially corresponds to the circuit arrangement 1 according to FIG. 1, but differs in that it has an additional storage device 8 that can be charged with a voltage U2 to emit a second voltage pulse. Therefore, this circuit arrangement 25 is suitable for applications in which two voltage pulses must be emitted in rapid succession. For example, it may be advantageous for the transfection of specific cell types to generate a short voltage pulse with a high field strength initially, followed immediately, preferably without any delay after termination of the first voltage pulse, by a second voltage pulse with a longer duration but a lower field strength. To this end, two high-voltage power supplies 5, 6 each feed a downstream storage device 7, 8, which each can, for example, comprise a capacitor or group of capacitors, which is/are each connected with a power semiconductor 9, 10 provided for emitting a voltage pulse or discharging the storage devices 7, 8. The power semiconductor 10 can here be actuated via the potential divider stage 12 by means of a voltage switch 14 via the controlling device 3, a control unit 22 and the controller 4. The storage devices 7, 8 are directly connected with the inputs of the power semiconductors 9, 10, wherein the storage devices 7, 8 can consist of one or more capacitors, depending on the used field strength and pulse duration. For example, the power semiconductor 9 can consist of an IGBT, and the power semiconductor 10 can consist of a MOSFET. However, both power semiconductors 9, 10 preferably consist of an IGBT. The output of the power semiconductor 10 is connected with the cuvette terminal 15 by means of a resistor 16 and a diode 17, so that no pulse can flow back via the second power semiconductor 10 if both power semiconductors 9, 10 are actuated simultaneously. To this end, the diode 17 is connected with the cuvette terminal 15 on the side of the cathode. A second control unit 22 can terminate actuation of the voltage switch 14 for the power semiconductor 10 via a switch 23. The applied voltage is routed to the control unit 22 via the resistor 16 in order to cut off the power if a maximum current is exceeded. Because the resistor 16 is disposed directly in the high-voltage circuit, the switch 23 is located behind the potential divider stage 12, so that no high-voltage pulses can get into the controlling device 3 and thus no danger is posed to the operating personnel. Depending on the intended purpose of the circuit arrangement 25, use can be made of one or more high-voltage power supplies 5, 6 with accompanying storage devices 7, 8 and necessary potential divider stages 11, 12 and voltage switches 13, 14 for actuating the power semiconductors 9, 10. The storage devices 7, 8 are here each equipped with one or more capacitors of the required capacity and breakdown voltage, so that a correspondingly high charge can be stored and transmitted to the cuvette terminal 15. With respect to controlling the discharge of the storage device 7 via the controller 4, the circuit arrangement 25 matches the circuit arrangement 1 according to FIG. 1 exactly.

Figure 3:
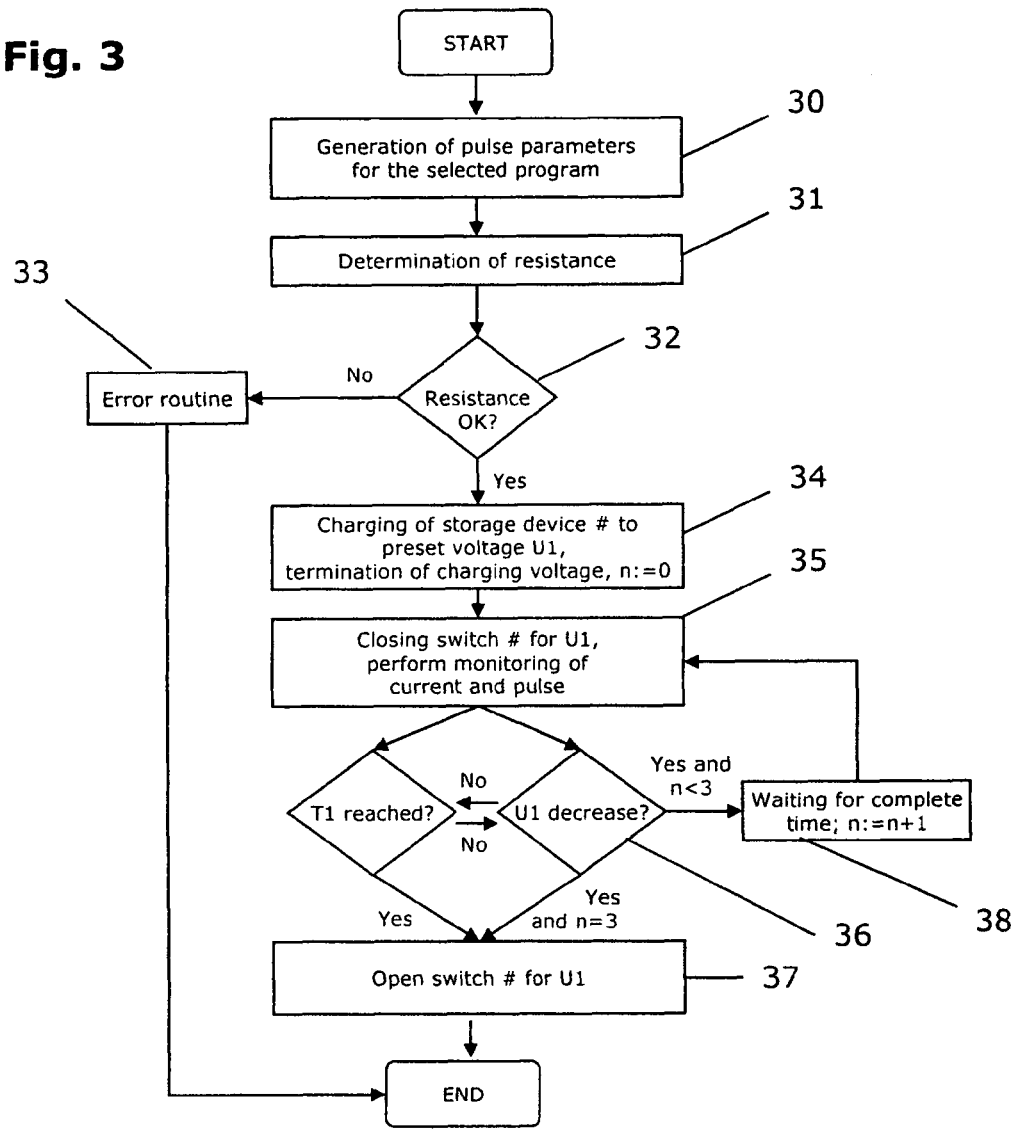
FIG. 3 is a flowchart to explain the method according to the invention.

FIG. 3 shows a schematic flowchart of the method according to a preferred embodiment of the invention. The necessary pulse parameters (e.g., pulse duration T1 and field strength) are first input via the adjustment unit or set by a readout from a memory card (not shown here). After the routine has been initiated (e.g., by actuating a corresponding trigger key), the pulse parameters for the selected program are first generated in step 30. In step 31, the ohm resistance of the cuvette is then determined by briefly applying a low voltage (e.g., 12 V) to the cuvette terminals, and then measuring the current (e.g., for 2 ms). As part of step 32, it is determined whether this resistance lies within a preset window. Should this not be the case, the routines are terminated by the error recovery routine 33. If the resistance lies duly within the preset window, the storage device 7 according to FIGS. 1 and 2 is charged to the preset voltage U1 in step 34. Once the desired charging voltage has been reached, charging by the high-voltage power supply is terminated. The emission of the first voltage pulse is then initiated in step 35 by closing the power semiconductor 9 according to FIGS. 1 and 2. This produces an electrical field in the cuvette, which accommodates the biomaterial to be treated. At the same time, the electrical parameters are monitored and tracked, e.g., the current rise via the control unit 20 according to FIGS. 1 and 2, and the chronological progression of the voltage pulse via the controller 4 according to FIGS. 1 and 2. A too steep rise of current is detected by the control unit 20 according to FIGS. 1 and 2, and for safety reasons causes the power semiconductor 9 according to FIGS. 1 and 2 to open immediately, and the routine to terminate (flank deactivation). This makes it possible to prevent lightning discharge. In this embodiment, the first voltage pulse is normally ended after a preset duration T1 which is processed in step 36. To this end, the power semiconductor is opened in step 37. However, if it is determined in step 36 that the duration T1 was not reached owing to a termination of the first voltage pulse as manifested in a voltage drop, the routine switches to step 38. Here, after a preset pause time, step 35 is once again called, thereby triggering an additional voltage pulse, wherein the controller 4 according to FIGS. 1 and 2 calculates and provides the duration of the additional voltage pulse (T2=T1−Tx). Another check is then performed in step 36 to determine whether the duration T1 (=Tx+T2) was reached. If this is the case, the routine switches to step 37, and ends the voltage pulse. By contrast, if the additional voltage pulse is also terminated, the routine again switches to step 38, so that another additional voltage pulse can be initiated. The number of repetitions, i.e., the maximum number of additional voltage pulses, is preset. In this exemplary embodiment, a maximum of three additional voltage pulses (n=3) can be initiated, so that the routine in step 36 switches to step 37 after a renewed termination of the third additional voltage pulse, and is finally ended.

Figure 4:
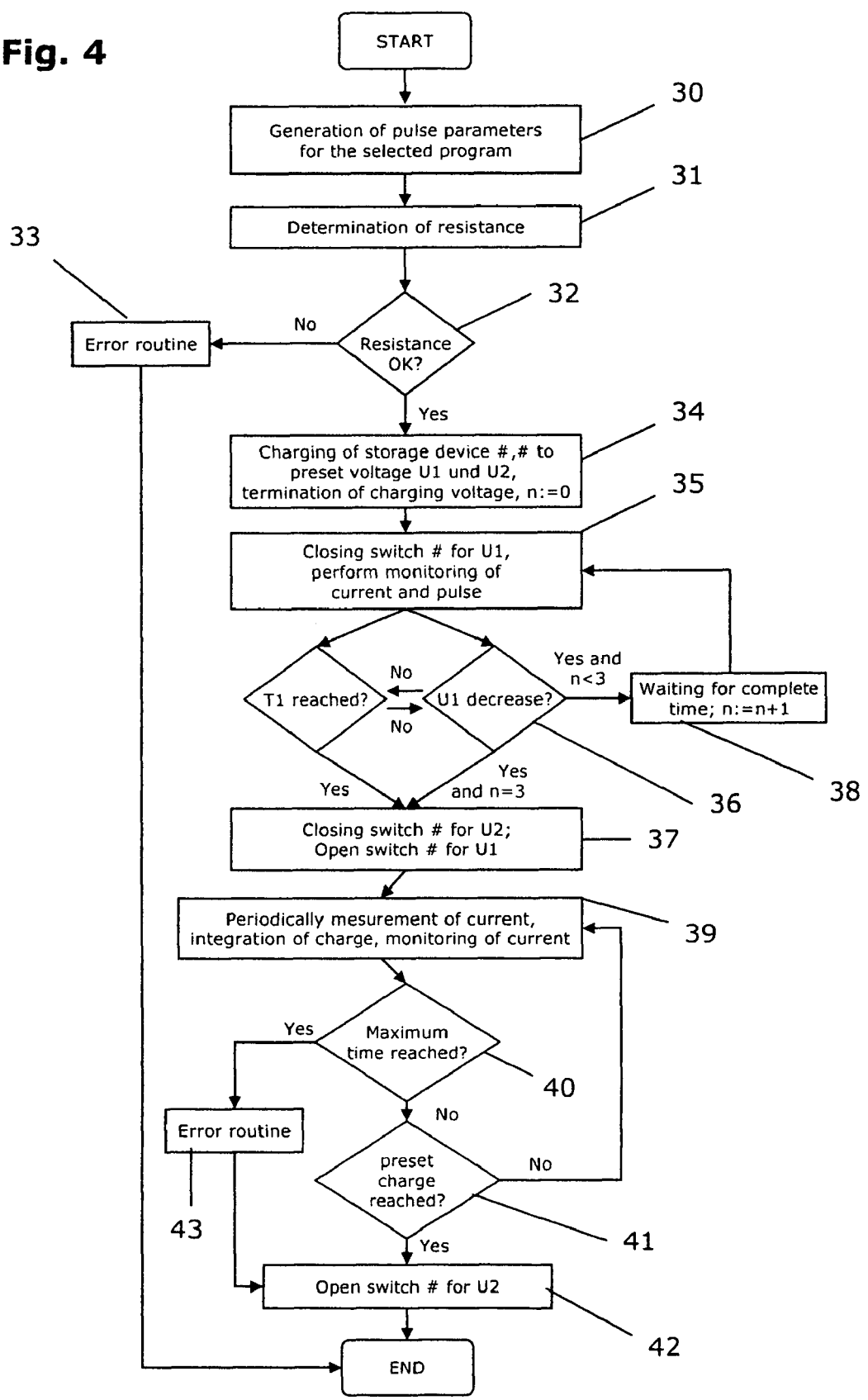
FIG. 4 is a flowchart to explain a special embodiment of the method according to the invention.

FIG. 4 shows a flowchart to explain a special embodiment of the method according to the invention, in which two merging voltage pluses are emitted. In the embodiment described here, a high-voltage pulse is ended after a preset period, and is immediately followed by a second pulse without interruption. Hence, the depicted method essentially corresponds to the method described on FIG. 34, except for step 38. The difference is that the second storage device 8 according to FIG. 2 is also charged to the preset voltage in step 34. Once the desired charging voltages have been reached, the corresponding high-voltage power supply terminates the charging process. In this special embodiment, the second power semiconductor 10 according to FIG. 2 is already closed in step 37 shortly before the first semiconductor 9 according to FIG. 2 is opened, resulting in a continuous transition between the two pulses. In the short time that both power semiconductors 9, 10 are simultaneously closed, the diode 17 according to FIG. 2 prevents a potentially higher voltage from being able to flow from the storage device 7 into the storage device 8. The power semiconductor 10 subsequently remains closed (unless opened by an excessive current via the control unit 22 until a preset charge Q has flowed through the cuvette 24 according to FIG. 2. To this end, the current flowing through the cuvette is measured and integrated in step 39 over preset time intervals (e.g., 1 ms). As soon as the prescribed setpoint charge has been reached (step 41) or a preset time has been exceeded (step 40), the power semiconductor 10 is opened in step 42, and the routine is ended. The capacity of the storage device 8 according to FIG. 2 is selected in such a way that the voltage gradually or slowly falls during the second pulse. If a disturbance prevents the prescribed setpoint charge from being reached even given a nearly completely discharged storage device, the process is terminated via the error recovery routine 43 after a correspondingly selected time limit has been exceeded.

Figure 5:
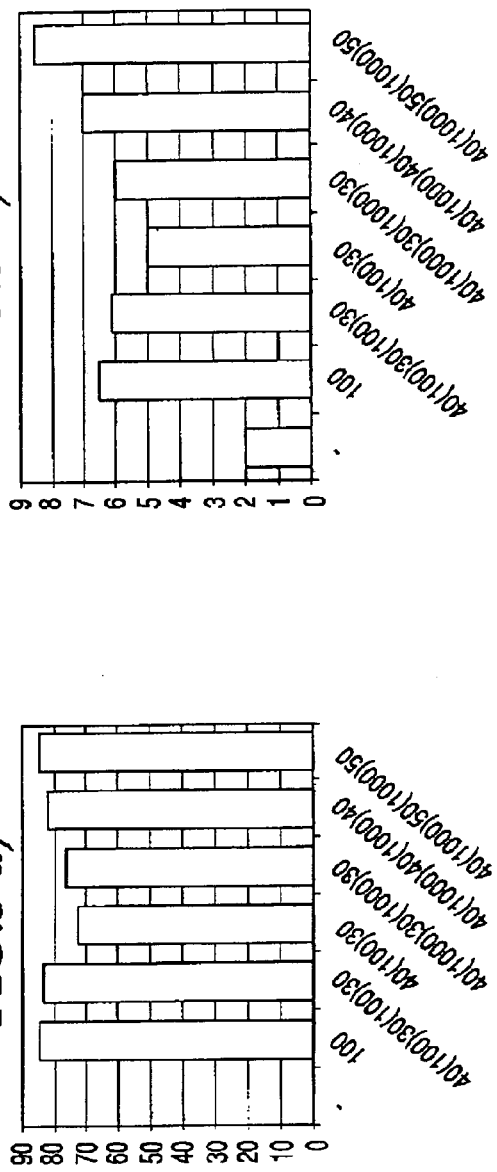
FIG. 5 shows diagrams with experimental data for artificially interrupted voltage pulses.
Figure 5:
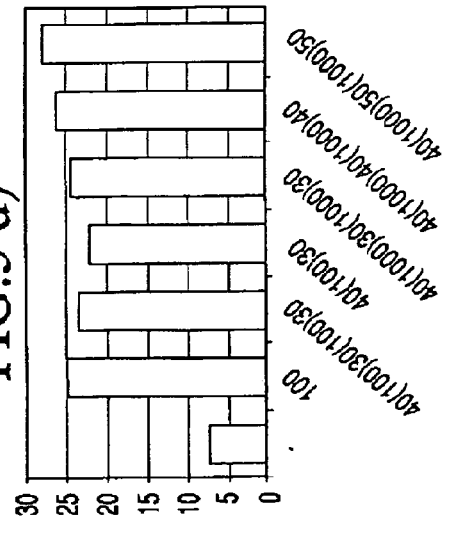
Figure 5:
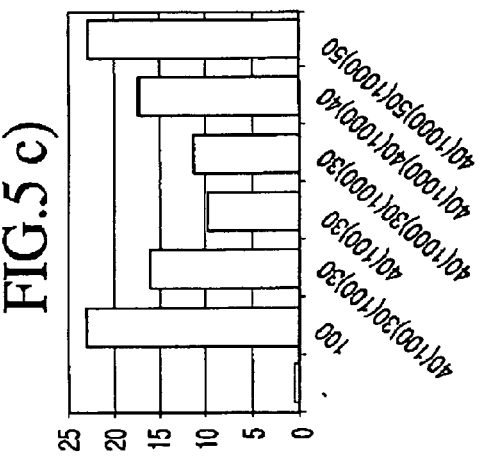

FIG. 5 shows diagrams of experimental data for artificially terminated voltage pulses.

To determine the data for FIGS. 5a and 5b, $1 \times 10^6$ K563 cells were introduced in a 100 µl solution of the Cell Line Nucleofector Kit R (amaxa GmbH), supplemented with 0.5 µg of pEGFP-C1 (Invitrogen) and subjected to a field of 5 kV/cm for varying times. The cells were subsequently placed in Iscove's modified Dulbecco's medium (Invitrogen) with 2 mM of GlutaMAX (Invitrogen), 100 µg/ml of Streptomycin, 100 U/ml of penicillin and 10% FCS (Sigma), and cultivated for 48 hours at 37° C. and 5% $CO_2$ in a moistened culture cabinet. The samples were then checked for GFP expression via flow cytometry (FACSCalibur, Becton Dickinson) and for viability via propidium iodide dyeing. The percentage shares of GFP expressing cells (a) and the percentage share of dead cells (b) are depicted. The bar labeling relates to the time switching of field exposition: all information is provided in µs, numbers stand for the pulse lengths, numbers in parenthesis stand for interspersed pauses.

FIG. 5a shows that the transfection efficiency of a complete first voltage pulse (T1=100 µs, bar 1: over 80%) can be approximately reached by continuing a first voltage pulse terminated after a time Tx=40 µs using additional voltage pulses (T2=30 µs and T3=30 µs, bar 2: over 80%). If the overall duration Ts=T2+T3 of the additional voltage pulses sums up to the duration T1 minus the time Tx lying between the beginning of the first voltage pulse and the termination thereof (Ts=T1−Tx=60 µs), and hence the preset duration T1=100 µs is reached as a whole, the transfection efficiency can be actually reproduced. By contrast, if T1=100 µs is not reached (Tx+T2=70 µs, bar 3: approx. 70%), the transfection efficiency cannot be completely reached. In these examples, the pause time between voltage pulses measured a respective 100 µs. At longer pauses (bars 4-6: 1000 µs), it apparently makes sense to select an overall duration Ts of the additional pulses that exceeds the duration T1 minus the time Tx lying between the beginning of the first voltage pulse and the termination thereof (Ts>T1−Tx), so as to achieve the transfection efficiency of the non-terminated first voltage pulse. However, the associated longer period for which the cells are exposed to the field is accompanied by an increased mortality rate (FIG. 5b).

To determine the data for FIGS. 5c and 5d, $1 \times 10^6$ PBMC from Buffy coats and 0.4 µg of pEGFP-C1 (Invitrogen) were brought into 100 µl solution from the Human T cell Nucleofector kit (amaxa GmbH). Analysis took place as described above after 20 hours of incubation and additional dyeing with an anti-CD3 antibody with coupling to phycoerythrin. Shown once again is the percentage share of transfected $CD3^+$-T-cells (c) as well as the percentage share of dead cells (relative to overall cells) (d). The bar labeling relates to the time switching of field exposition: all information is provided in µs, numbers stand for the pulse lengths, numbers in parenthesis stand for interspersed pauses.

FIGS. 5c and 5d confirm the results of the tests depicted on FIGS. 5a and 5b; wherein the transfection efficiencies are lower overall, so that larger fluctuations come about. It is here demonstrated as well that a terminated first voltage pulse can be successfully continued. In this case, the test result can be clearly improved given longer pauses if the selected overall duration Ts of the additional voltage pulses exceeds T1−Tx.

LIST OF REFERENCE NUMERALS

1 Circuit arrangement
2 Adjustment unit
3 Controlling device
4 Controller
5 High-voltage power supply
6 High-voltage power supply
7 Storage device
8 Storage device
9 Power semiconductor
10 Power semiconductor
11 Potential divider stage
12 Potential divider stage
13 Voltage switch 14 Voltage switch
15 Cuvete terminal
16 Resistor
17 Diode
18 Cuvette terminal
19 Resistor
20 Control unit
21 Switching device
22 Control unit
23 Switch
24 Cuvette
25 Circuit arrangement
30 –
43 Steps

What is claimed is:

1. A method for treating biomaterial comprising:
 (a) providing at least one electrical field generated by a first voltage pulse, and
 (b) once the value for an electrical parameter has exceeded or dropped below a preset limit, terminating the first voltage pulse,
  wherein the first voltage pulse is continued after said terminating by at least one additional voltage pulse,
  wherein a specific duration T1 is preset for the first voltage pulse
  and wherein the first voltage pulse is terminated after time Tx, and a duration T2 of the at least one additional voltage pulse is at least equal to the duration T1 minus said time Tx lying between a beginning of the first voltage pulse and termination thereof.

2. The method according to claim 1, wherein the duration T1 ranges from 10 μs to 1 ms.

3. The method according to claim 1, wherein a field strength preset for the additional voltage pulse equals a field strength for the first voltage pulse.

4. The method according to claim 3, wherein said preset field strength is 2 to 10 KV/cm.

5. The method according to claim 1, wherein a specific pause time is preset between termination of the first voltage pulse and generation of the additional voltage pulse.

6. The method according to claim 5, wherein the pause time is at least 40 μs.

7. The method according to claim 1, wherein a total of at least two additional voltage pulses are generated if the preceding additional voltage pulse(s) are terminated.

8. The method according to claim 7, wherein a specific duration T1 is preset for the first voltage pulse, and an overall duration Ts of the additional voltage pulse(s) is at least equal to the duration T1 minus time Tx lying between a beginning of the first voltage pulse and termination thereof.

9. The method according to claim 1, wherein a program element, read and executed via an electronic data processor, performs the method.

10. The method of claim 9, wherein said program element is stored on a storage medium which can be read via an electronic data processor.

* * * * *